US009175944B2

(12) United States Patent
Kang et al.

(10) Patent No.: US 9,175,944 B2
(45) Date of Patent: Nov. 3, 2015

(54) DURABLE SINGLE MODE FIBER PROBE WITH OPTIMIZED REFERENCE REFLECTIVITY

(71) Applicant: The Johns Hopkins University, Baltimore, MD (US)

(72) Inventors: Jin U. Kang, Ellicott City, MD (US); Xuan Liu, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 256 days.

(21) Appl. No.: 13/709,958

(22) Filed: Dec. 10, 2012

(65) Prior Publication Data

US 2014/0160485 A1   Jun. 12, 2014

(51) Int. Cl.
*G01B 9/02*        (2006.01)
*A61B 3/10*        (2006.01)
*A61B 5/00*        (2006.01)
*G02B 6/10*        (2006.01)
*G02B 6/06*        (2006.01)

(52) U.S. Cl.
CPC ............ *G01B 9/02052* (2013.01); *A61B 3/102* (2013.01); *G01B 9/02091* (2013.01); *A61B 5/0066* (2013.01); *A61B 5/0073* (2013.01); *A61B 5/0084* (2013.01); *G02B 6/06* (2013.01); *G02B 6/10* (2013.01); *Y10T 156/108* (2015.01)

(58) Field of Classification Search
CPC .......... G02B 6/06; G02B 6/10; A61B 5/0066; A61B 5/0073; A61B 5/0084
USPC ................................... 385/116; 606/1, 13–16
See application file for complete search history.

(56) References Cited

U.S. PATENT DOCUMENTS

| | | | | |
|---|---|---|---|---|
| 5,830,138 A * | 11/1998 | Wilson | ......................... | 600/327 |
| 6,231,568 B1 * | 5/2001 | Loeb et al. | ..................... | 606/15 |
| 6,564,087 B1 * | 5/2003 | Pitris et al. | .................... | 600/478 |
| 7,848,791 B2 * | 12/2010 | Schmitt et al. | ................ | 600/476 |
| 8,582,934 B2 * | 11/2013 | Adler et al. | ..................... | 385/33 |

(Continued)

FOREIGN PATENT DOCUMENTS

WO   WO-00/42906 A2   7/2000
WO   WO-2011/15627 A1   2/2011

OTHER PUBLICATIONS

International Search Report and Written Opinion issued in PCT Application No. PCT/US2013/074143 dated Mar. 26, 2014.

(Continued)

*Primary Examiner* — Ryan Lepisto
*Assistant Examiner* — Guy Anderson
(74) *Attorney, Agent, or Firm* — Venable LLP; Henry J. Daley; Laura G. Remus

(57) ABSTRACT

A probe for a common path optical coherence tomography system includes a sheath having a proximal end and a distal end and defining a lumen therein, a single mode optical fiber disposed within the lumen of the sheath such that a portion of the single mode optical fiber extends beyond the distal end of the sheath. The single mode optical fiber has an end face for transmitting and receiving light. The probe also includes a layer of hardened epoxy encasing the portion of the single mode optical fiber that extends beyond the distal end of the sheath except for the end face. The single mode optical fiber has an optical axis extending along a longitudinal direction of the single mode optical fiber. The hardened epoxy is polished at a non-orthogonal angle relative to the optical axis at the end face.

14 Claims, 4 Drawing Sheets

(56) References Cited

U.S. PATENT DOCUMENTS

| | | | |
|---|---|---|---|
| 2005/0261568 A1* | 11/2005 | Hular et al. | 600/407 |
| 2005/0283135 A1 | 12/2005 | Pepin | |
| 2008/0306391 A1* | 12/2008 | Hular et al. | 600/478 |
| 2009/0247878 A1* | 10/2009 | Tanioka et al. | 600/462 |
| 2010/0253949 A1* | 10/2010 | Adler et al. | 356/479 |
| 2011/0098572 A1* | 4/2011 | Chen et al. | 600/463 |
| 2012/0116234 A1* | 5/2012 | Farcy et al. | 600/478 |
| 2012/0220883 A1 | 8/2012 | Manstrom et al. | |

OTHER PUBLICATIONS

Balicki et al., "Single fiber optical coherence tomography microsurgical instruments for computer and robot-assisted retinal surgery," Proceedings of the MICCAI Conference, London, 108-115 (2009).

Li et al., Jae-Ho Han, Xuan Liu, and Jin U. Kang, "Signal-to-noise ratio analysis of all-fiber common-path optical coherence tomography," Appl. Opt. 47, 4833-4840 (2008).

Liu, Yong Huang, and Jin U. Kang, "Distortion-free freehand-scanning OCT implemented with real-time scanning speed variance correction," Opt. Express 20, 16567-16583 (Jul. 2012).

Rollins et al., "Optimal interferometer designs for optical coherence tomography," Opt. Lett. 24, 1484-1486 (1999).

* cited by examiner

DURABLE SINGLE MODE FIBER PROBE WITH OPTIMIZED REFERENCE REFLECTIVITY

This invention was made with Government support of Grant Nos. R01 EY021540 and 1R01 EB 007969-01, awarded by the Department of Health and Human Services, The National Institutes of Health (NIH). The U.S. Government has certain rights in this invention.

BACKGROUND

1. Field of Invention

The field of the currently claimed embodiments of this invention relates to optical coherence tomography (OCT) systems, and more particularly to durable single mode optical fiber probes for OCT systems and OCT systems that incorporate the probes.

2. Discussion of Related Art

Common-path (CP) interferometer based optical coherence tomography (OCT) systems can use a single mode fiber (SMF) probe to serve as both reference and sample arms [1]. This configuration allows a CP ultra-thin probe to be integrated with standard surgical instruments to provide various sensing functionalities such as force sensing or depth ranging in intra-operative settings [2]. Usually, the cleaved fiber tip provides reference light derived from Fresnel reflection; and the reference light interferes with sample light. However, a bare fiber tip without external protection can be very fragile. In addition, once the tip of a bare fiber probe is contaminated during a surgical procedure, it is very challenging to clean the fiber tip without damaging it. Another drawback of bare fiber probe in CP OCT systems is that the reference power level is not optimal to achieve high signal to noise ratio (SNR) [3, 4]. The reference power is determined by the refractive indices of glass and the media where the probe is operated. Therefore, the reference power level cannot be adjusted as in an OCT system based on a Michelson interferometer. There thus remains a need for improved probes for OCT systems, and OCT systems that incorporate the probes.

SUMMARY

A probe for a common path optical coherence tomography system according to an embodiment of the current invention includes a sheath having a proximal end and a distal end and defining a lumen therein, a single mode optical fiber disposed within the lumen of the sheath such that a portion of the single mode optical fiber extends beyond the distal end of the sheath. The single mode optical fiber has an end face for transmitting and receiving light. The probe also includes a layer of hardened epoxy encasing the portion of the single mode optical fiber that extends beyond the distal end of the sheath except for the end face. The single mode optical fiber has an optical axis extending along a longitudinal direction of the single mode optical fiber. The hardened epoxy is polished at a non-orthogonal angle relative to the optical axis at the end face.

An optical coherence tomography system according to an embodiment of the current invention includes a fiber-optic sensor system, a light source optically coupled to the fiber-optic sensor system, and a detection system optically coupled to the fiber-optic sensor system. The fiber-optic sensor system includes an optical probe. The optical probe includes a sheath having a proximal end and a distal end and defining a lumen therein, a single mode optical fiber disposed within the lumen of the sheath such that a portion of the single mode optical fiber extends beyond the distal end of the sheath. The single mode optical fiber has an end face for transmitting and receiving light. The probe also includes a layer of hardened epoxy encasing the portion of the single mode optical fiber that extends beyond the distal end of the sheath except for the end face. The single mode optical fiber has an optical axis extending along a longitudinal direction of the single mode optical fiber. The hardened epoxy is polished at a non-orthogonal angle relative to the optical axis at the end face.

A method of producing a probe for a common path optical coherence tomography system according to an embodiment of the current invention includes obtaining a sheath having a proximal end and a distal end, the sheath defining a lumen therein; disposing a single mode optical fiber within the lumen of the sheath such that a portion of the single mode optical fiber extends beyond the distal end of the sheath, the single mode optical fiber having an end face for transmitting and receiving light and an optical axis extending along a longitudinal direction of the single mode optical fiber; applying a layer of ultraviolet-light curable epoxy on the portion of the single mode optical fiber that extends beyond the distal end of the sheath; exposing the ultraviolet-light curable epoxy to ultraviolet light such that the ultraviolet-light curable epoxy cures to become hardened; prior to applying the epoxy, trimming some of the portion of the single mode optical fiber that extends beyond the distal end of the sheath to provide an end face of the single mode optical fiber; and polishing the epoxy tip to a non-orthogonal angle relative to the optical axis at the end face.

BRIEF DESCRIPTION OF THE DRAWINGS

Further objectives and advantages will become apparent from a consideration of the description, drawings, and examples.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

The term "light" as used herein is intended to have a broad meaning that can include both visible and non-visible regions of the electromagnetic spectrum. For example, visible, near infrared, infrared and ultraviolet light are all considered as being within the broad definition of the term "light."

To address these and other problems associated with SMF probes, we protected the fiber tip with ultraviolet (UV) curable epoxy and polished the fiber tip to adjust the reference power level. With UV curable epoxy protection, the fiber probe becomes durable and can be cleaned conveniently with a typical fiber connector cleaner. The fiber tip covered with hardened epoxy is afterwards polished by a high precision fiber polisher. Instead of being polished to be normal to the fiber axis, the fiber tip is slightly angle polished. By adjusting the polishing angle, the reference power can be optimized to achieve improved SNR.

Probe Fabrication

Figure 1A:
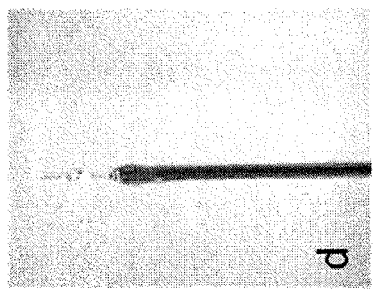
FIGS. 1A-1G show an example of a probe for a common path optical coherence tomography system and methods of manufacture according to some embodiments of the current invention.
Figure 1B:
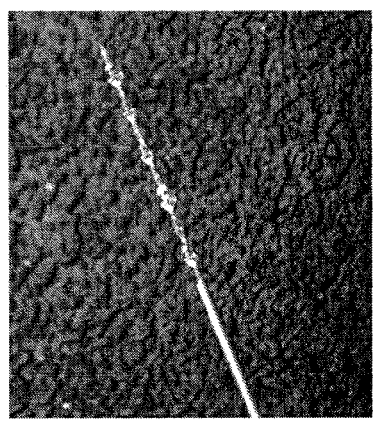
Figure 1C:
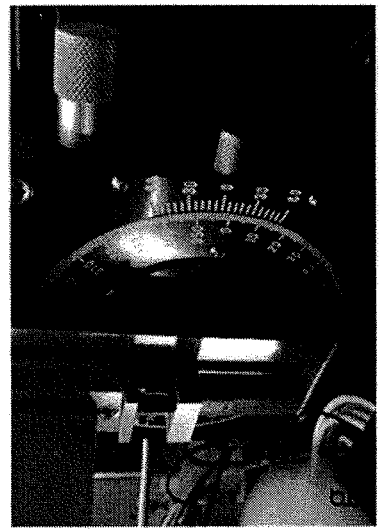
Figure 1D:
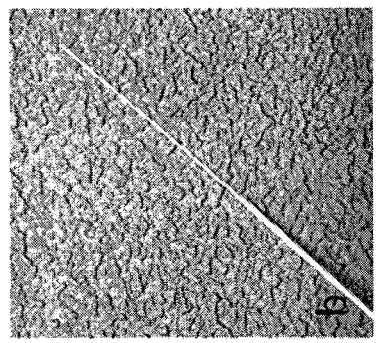
Figure 1E:
Figure 1F:
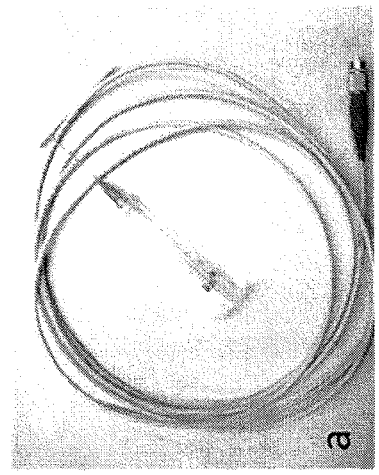
Figure 1G:
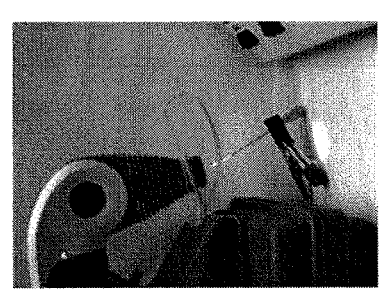

To fabricate a durable SMF probe with optimized reference reflectivity, we first strip the plastic jacket of a SMF and insert it into a flat top stainless steel needle that provides mechanical rigidity for the probe (FIGS. 1A and 1B). The fiber tip is pulled out and excess fiber is removed. There remains a short segment of fiber (less than 1 mm) that is outside of the needle. High viscosity UV curable epoxy is then applied to the fiber that is outside of the needle (FIG. 1C). With epoxy attached, we recess the fiber slightly and the epoxy forms a spherical crown at the top of the needle (FIG. 1D). Afterwards, the epoxy is cured with UV light source (FIG. 1D). However, such a probe tip cannot be easily damaged because it is surrounded by hardened epoxy. The probe tip is then polished to an angle that optimizes the SNR of OCT image with a high precision polisher (FIGS. 1F and 1G).

FIGS. 1A-1G show a probe for a common path optical coherence tomography system according to an embodiment of the current invention. The probe includes a sheath having a proximal end and a distal end and defining a lumen therein, and a single mode optical fiber disposed within the lumen of the sheath such that a portion of the single mode optical fiber that extends beyond the distal end of the sheath. The single mode optical fiber has an end face for transmitting and receiving light. The probe further includes a layer of hardened epoxy encasing the portion of the single mode optical fiber that extends beyond the distal end of the sheath except for the end face. The single mode optical fiber has an optical axis extending along a longitudinal direction of the single mode optical fiber and the end face of the single mode optical fiber is polished at a non-orthogonal angle relative to the optical axis at the end face.

In some embodiments, the non-orthogonal angle can be at least 1° relative to a normal to the optical axis at the end face and less than 5° relative to the normal. In some embodiments, the non-orthogonal angle can be at least 1° relative to a normal to the optical axis at the end face and less than 4° relative to the normal. In some embodiments, the non-orthogonal angle is about 3° relative to a normal to the optical axis at the end face.

In some embodiments, the hardened epoxy can be ultraviolet-light curable epoxy. In some embodiments, the sheath can be, but is not limited to, a stainless steel needle.

Figure 2:
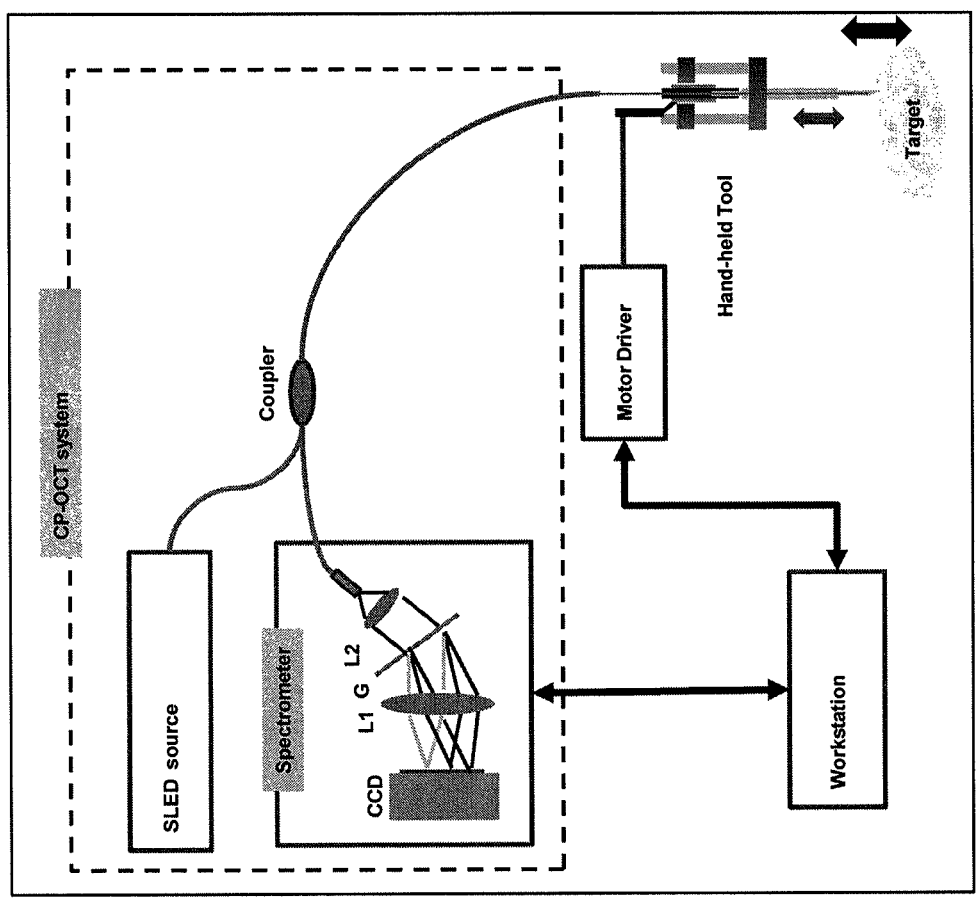
FIG. 2 is a schematic illustration of a CP-OCT system that includes a probe according to an embodiment of the current invention.

FIG. 2 provides a schematic illustration of a CP-OCT system that can include a probe according to an embodiment of the current invention. The CP-OCT system of the example in FIG. 2 includes a fiber-optic sensor system, a light source optically coupled to the fiber-optic sensor system, and a detection system optically coupled to the fiber-optic sensor system. The example of FIG. 2 includes the probe incorporated into a motorized hand-held tool. However the general concepts of the current invention are not limited to this one example.

Another embodiment of the current invention is directed to a method of producing a probe for a common path optical coherence tomography system. This method includes obtaining a sheath having a proximal end and a distal end, the sheath defining a lumen therein; and disposing a single mode optical fiber within the lumen of the sheath such that a portion of the single mode optical fiber extends beyond the distal end of the sheath. The single mode optical fiber has an end face for transmitting and receiving light and an optical axis extending along a longitudinal direction of the single mode optical fiber. This method further includes applying a layer of ultraviolet-light curable epoxy on the portion of the single mode optical fiber that extends beyond the distal end of the sheath; exposing the ultraviolet-light curable epoxy to ultraviolet light such that the ultraviolet-light curable epoxy cures to become hardened; trimming some of the portion of the single mode optical fiber that extends beyond the distal end of the sheath to provide an end face of the single mode optical fiber prior to applying the epoxy; and polishing the end of the probe to a non-orthogonal angle relative to the optical axis at said end face.

In some embodiments, the non-orthogonal angle can be at least 1° relative to a normal to the optical axis at the end face and less than 5° relative to the normal. In some embodiments, the non-orthogonal angle can be at least 1° relative to a normal to the optical axis at the end face and less than 4° relative to the normal. In some embodiments, the non-orthogonal angle is about 3° relative to a normal to the optical axis at the end face.

Further additional concepts and embodiments of the current invention will be described by way of the following examples. However, the broad concepts of the current invention are not limited to these particular examples.

EXAMPLES

Figure 3:
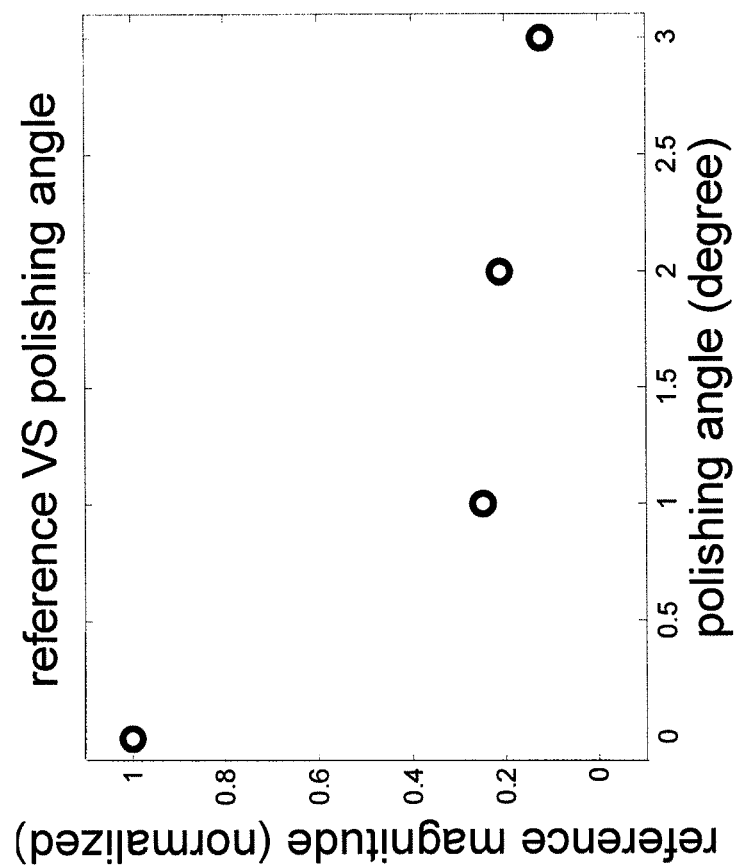
FIG. 3 provides data for reference level at different SMF polishing angles.
Figures 4A, 4B, 4C, 4D:
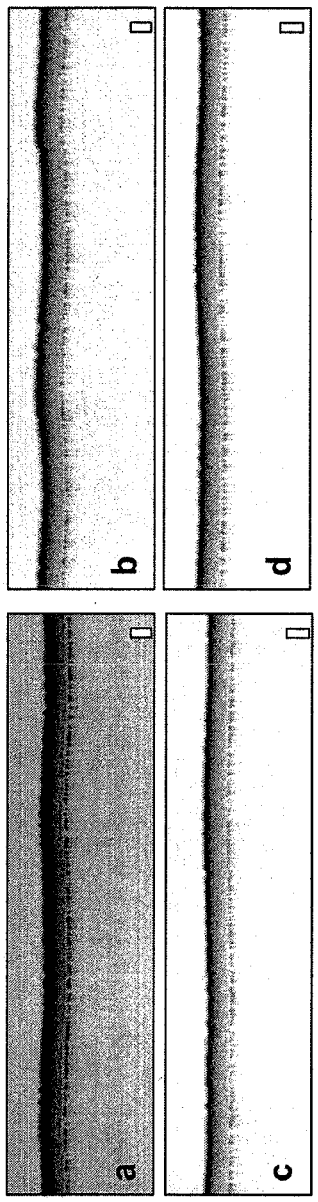
FIGS. 4A-4D show OCT images of fiber polishing paper with SMF probe polished at 0 (a), 1 (b), 2 (c), and 3 (d) degrees.
Figures 5A, 5B:
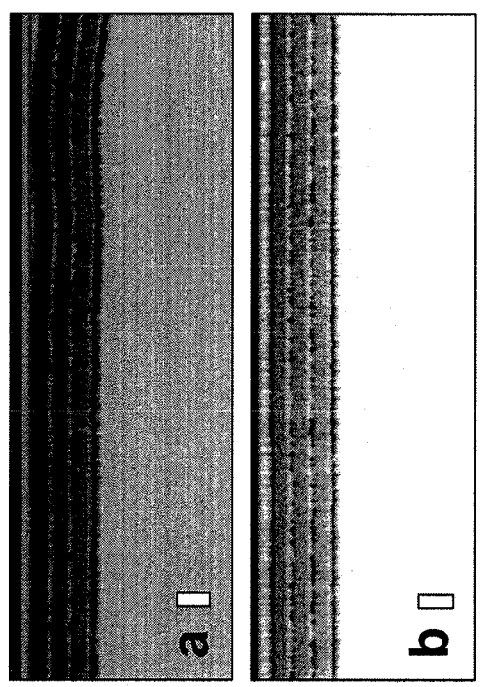
FIGS. 5A-5B show OCT images of multiple layers of tape, obtained with SMF probe polished at 0 (a) and 3 (b) degrees.

For the same SMF, the reference power levels were obtained by averaging count reading from the CCD camera and normalized to the reference power level with 0 degree polishing, as shown in FIG. 3. Throughout these examples, the polishing angle is referred to the plane normal to fiber longitudinal axis. With angle polishing, the reference power decreases significantly. The SNR improvement can be observed in FIGS. 4A-4D and 5A-5B. FIGS. 4A-4D show the cross-sectional images of the fiber polishing paper, obtained with the same SMF polished at different angle. FIGS. 4A-4D correspond to polishing angle 0, 1, 2 and 3 degree, respectively. Scale bars in FIGS. 4A-4D indicate 100 μm optical length. Images in FIGS. 4A-4D are displayed with the same dynamic range for a fair comparison. Clearly, FIGS. 4B-4D have better SNR performance than FIG. 4A. Similarly, we show OCT images of multi-layered phantom in FIGS. 5A and 5B obtained with SMF probe polished at 0 and 3 degrees. The phantom consisted of three layers of tapes. With higher SNR, FIG. 5B demonstrates better image quality as compared to FIG. 5A.

REFERENCES

[1] Xuan Liu, Yong Huang, and Jin U. Kang, "Distortion-free freehand-scanning OCT implemented with real-time scanning speed variance correction," Opt. Express 20, 16567-16583 (2012)

[2] M. Balicki, J. Han, I. Iordachita, P. Gehlbach, J. Handa, J. U. Kang, and R. Taylor, "Single fiber optical coherence tomography microsurgical instruments for computer and robot-assisted retinal surgery," Proceedings of the MICCAI Conference, London, 108-115 (2009)

[3] Xiaolu Li, Jae-Ho Han, Xuan Liu, and Jin U. Kang, "Signal-to-noise ratio analysis of all-fiber common-path optical coherence tomography," Appl. Opt. 47, 4833-4840 (2008)

[4] Andrew M. Rollins and Joseph A. Izatt, "Optimal interferometer designs for optical coherence tomography," Opt. Lett. 24, 1484-1486 (1999)

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A probe for a common path optical coherence tomography system, comprising:
   a sheath having a proximal end and a distal end, said sheath defining a lumen therein;
   a single mode optical fiber disposed within said lumen of said sheath such that a portion of said single mode optical fiber extends beyond said distal end of said sheath, said single mode optical fiber having an end face for transmitting and receiving light; and
   a layer of hardened epoxy encasing said portion of said single mode optical fiber that extends beyond said distal end of said sheath except for said end face,
   wherein said single mode optical fiber has an optical axis extending along a longitudinal direction of said single mode optical fiber, and
   wherein said hardened epoxy is polished at a non-orthogonal angle relative to said optical axis at said end face, and
   wherein said non-orthogonal angle is at least 1° relative to a normal to said optical axis at said end face and less than 5° relative to said normal.

2. A probe for a common path optical coherence tomography system according to claim 1, wherein said non-orthogonal angle is at least 1° relative to a normal to said optical axis at said end face and less than 4° relative to said normal.

3. A probe for a common path optical coherence tomography system according to claim 1, wherein said non-orthogonal angle is about 3° relative to a normal to said optical axis at said end face.

4. A probe for a common path optical coherence tomography system according to claim 1, wherein said hardened epoxy is ultraviolet-light curable epoxy.

5. A probe for a common path optical coherence tomography system according to claim 4, wherein said sheath is a stainless steel needle.

6. An optical coherence tomography system, comprising:
   a fiber-optic sensor system;
   a light source optically coupled to said fiber-optic sensor system; and
   a detection system optically coupled to said fiber-optic sensor system,
   wherein said fiber-optic sensor system comprises an optical probe, comprising:
      a sheath having a proximal end and a distal end, said sheath defining a lumen therein,
      a single mode optical fiber disposed within said lumen of said sheath such that a portion of said single mode optical fiber that extends beyond said distal end of said sheath, said single mode optical fiber having an end face for transmitting and receiving light, and
      a layer of hardened epoxy encasing said portion of said single mode optical fiber that extends beyond said distal end of said sheath except for said end face,
   wherein said single mode optical fiber has an optical axis extending along a longitudinal direction of said single mode optical fiber, and
   wherein said hardened epoxy is polished at a non-orthogonal angle relative to said optical axis at said end face,
   wherein said non-orthogonal angle is at least 1° relative to a normal to said optical axis at said end face and less than 5° relative to said normal.

7. An optical coherence tomography system according to claim 6, wherein said non-orthogonal angle is at least 1° relative to a normal to said optical axis at said end face and less than 4° relative to said normal.

8. An optical coherence tomography system according to claim 6, wherein said non-orthogonal angle is about 3° relative to a normal to said optical axis at said end face.

9. An optical coherence tomography system according to claim 6, wherein said hardened epoxy is ultraviolet-light curable epoxy.

10. An optical coherence tomography system according to claim 9, wherein said sheath is a stainless steel needle.

11. A method of producing a probe for a common path optical coherence tomography system, comprising: obtaining a sheath having a proximal end and a distal end, said sheath defining a lumen therein; disposing a single mode optical fiber within said lumen of said sheath such that a portion of said single mode optical fiber extends beyond said distal end of said sheath, said single mode optical fiber having an end face for transmitting and receiving light and an optical axis extending along a longitudinal direction of said single mode optical fiber; applying a layer of ultraviolet-light curable epoxy on said portion of said single mode optical fiber that extends beyond said distal end of said sheath; exposing said ultraviolet-light curable epoxy to ultraviolet light such that said ultraviolet-light curable epoxy cures to become hardened; prior to applying the epoxy, trimming some of said portion of said single mode optical fiber that extends beyond said distal end of said sheath to provide an end face of said single mode optical fiber; and polishing said epoxy tip to a non-orthogonal angle relative to said optical axis at said end face, and wherein said non-orthogonal angle is at least 1° relative to a normal to said optical axis at said end face and less than 5° relative to said normal.

12. A method of producing a probe for a common path optical coherence tomography system according to claim 11, wherein said non-orthogonal angle is at least 1° relative to a normal to said optical axis at said end face and less than 4° relative to said normal.

13. A method of producing a probe for a common path optical coherence tomography system according to claim 11, wherein said non-orthogonal angle is about 3° relative to a normal to said optical axis at said end face.

14. A method of producing a probe for a common path optical coherence tomography system according to claim 11, wherein said sheath is a stainless steel needle.

* * * * *